United States Patent

Kneller et al.

[11] Patent Number: 5,023,000
[45] Date of Patent: Jun. 11, 1991

[54] OLIGOMER-CONTAINING PHOSPHATE SCALE INHIBITORS

[75] Inventors: James F. Kneller, LaGrange Park; Barbara E. Fair, Downers Grove, both of Ill.; Gianfranco F. Mazzani; I. Sergio Di Simone, both of Roma, Italy

[73] Assignee: Nalco Chemical Company, Naperville, Ill.

[21] Appl. No.: 521,627

[22] Filed: May 10, 1990

[51] Int. Cl.$^5$ ................................. C02F 5/14
[52] U.S. Cl. .................... 210/697; 210/699; 252/180; 252/181
[58] Field of Search .................. 210/698–701, 210/697; 252/180, 181

[56] References Cited

U.S. PATENT DOCUMENTS

| | | | |
|---|---|---|---|
| 4,088,574 | 5/1978 | Quinlan | 210/700 |
| 4,088,678 | 5/1978 | Matt et al. | 252/180 |
| 4,253,969 | 3/1981 | Becker et al. | 210/699 |
| 4,372,870 | 2/1983 | Snyder et al. | 252/180 |
| 4,913,823 | 4/1990 | Lipinski et al. | 252/180 |

FOREIGN PATENT DOCUMENTS 1521440 8/1978 United Kingdom .

*Primary Examiner*—Peter Hruskoci
*Attorney, Agent, or Firm*—John G. Premo; Robert A. Miller

[57] ABSTRACT

Calcium carbonate scale is controlled by treating calcium carbonate containing waters with a predominantly phosphinate containing composition where has as its major ingredient more than 32 mole percent of a phosphinicosuccinic acid oligomer having the probable structural formula .

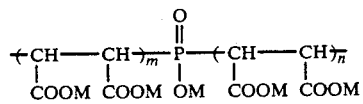

M is H, Na, K, NH$_4$, or mixtures thereof; and m and n are either 0 or a small whole number with proviso that either m or n is a small whole number and the sum of m plus n is greater than 2.

3 Claims, No Drawings

OLIGOMER-CONTAINING PHOSPHATE SCALE INHIBITORS

INTRODUCTION

The term "cooling water" is applied wherever water is circulated through equipment to absorb and carry away heat. This definition includes air conditioning systems, engine jacket systems, refrigeration systems, as well as the multitude of industrial heat exchange operations, such as found in oil refineries, chemical plants, steel mills, etc.

The once-through system, as the name implies, is one in which the water is passed through the heat exchange equipment and the cooling water is then discharged to waste. Usually, a once-through system is employed only where water at suitably low temperature is readily available in large volume and at low cost. The usual source of once-through cooling water is from wells, rivers, and lakes, where the cost involved is that of pumping only. In a once-through system, no evaporation takes place and consequently the water does not concentrate. Circulating water characteristics are the same as the makeup water.

The use of a recirculating system, in which a cooling tower, spray pond, evaporative condenser, and the like serve to dissipate heat, permits great economy in makeup water requirements. With dwindling supplies of fresh cold water available for industry's cooling requirements, increased use must be made of recirculating systems in which the cooling water is used over and over again. After passage of the circulating water through the heat exchange equipment, the water is cooled in passing over the cooling tower. This cooling effect is produced by evaporation of a portion of the circulating water in passing over the tower. By virtue of the evaporation which takes place in cooling, the dissolved solids and suspended solids in the water become concentrated.

The circulating water becomes more concentrated than the makeup water due to this evaporation loss. Cycles of concentration is the term employed to indicate the degree of concentration of the circulating water as compared with the makeup. For example, 2.0 cycles of concentration indicates the circulating water is twice the concentration of the makeup water.

The precipitation of calcium carbonate and calcium phosphate may form scale, particularly on heat exchange surfaces. In general, the term "scale" applies to deposits which result from crystallization or precipitation of salts from solution. Some of the factors which affect scale formation are temperature, rate of heat transfer, pH and alkalinity of the water, and concentration of ions including calcium, sulfate, magnesium, silica, and phosphate.

In the past, in order to minimize the formation of the scale forming salts, the cooling water systems were operated at pHs where the solubility of the "hardness" or "scale forming" ions was the greatest. Because the pHs of the systems were acidic, corrosion inhibitors, together with dispersants, were the normal treatment. With the advent of tight controls as regards toxic pollutant discharge, operating parameters of cooling water systems had to be changed in an attempt to utilize non-chromate treatment. The development of high pH and/or non-chromate corrosion programs over the past few years has concurrently enhanced the potential for heat exchange fouling due to chemical precipitation.

Most of the currently used scale preventative treatments include phosphate and/or phosphonic acid compounds such as the alkali metal polyphosphates, organophosphates, e.g., phosphate esters, etc., amino-trimethylene phosphonic acid, hydroxy ethylidene disphosphonic acid, and the water-soluble salts thereof.

Many of the organophosphorus compositions used as scale control agents are effective, but suffer from the drawback that they are relatively expensive to use. This is usually due to the costly synthetic methods used to produce them. Relatively inexpensive organophosphorus scale inhibiting compositions are those disclosed in U.S. Pat. No. 4,088,678. This patent purports to disclose a method for the preparation of monosodium phosphinicobis(succinic acid). It also purports to show this compound as possessing activity as a scale inhibitor. The same concepts are shown in more detail in its British counterpart, GB No. 1,521,440. The disclosures of these patents are incorporated herein by reference.

Both patents teach preparing its phosphinicobis(succinate) composition by reacting maleic acid with sodium hypophosphite in the presence of a water-soluble initiator. The patents demonstrate that the optimum molar ratio of maleic acid to the hypophosphite is 2.2. They clearly indicate that further excesses of the maleic acid do not result in an improved product.

Duplicating the experimental work described in the U.S. and British patents resulted in our discovery. In the first instance, it was ascertained the products formed using a molar ratio of maleic acid to hypophosphite of 2.0 were, in fact, mixtures of products. Secondly, the active component that prevents scale formation is an oligomeric species. Finally, if the oligomeric species are not present in the compositions, there is poor scale inhibition or chelation.

THE INVENTION

The invention comprises a method for generally controlling the deposition of scale and particularly controlling calcium carbonate scale on the structural parts of a system exposed to an aqueous medium containing calcium carbonate under deposit forming conditions which method comprises adding to the aqueous medium an effective amount of a predominantly phosphinate-containing composition comprising:

| Ingredients | Mole Percent - Less Than |
|---|---|
| A. Monosodium phosphinicobis-(succinic acid) | 22 |
| B. Monosodium phosphinicosuccinic acid | 26 |
| C. Sodium phosphonosuccinic acid | 12 |
| D. Sodium phosphate | 5 |
| E. Sodium phosphite | 6 |
| F. Sodium hypophosphite, and | 6 |
| G. A phosphinicosuccinic acid oligomer having the probable structural formula: | |

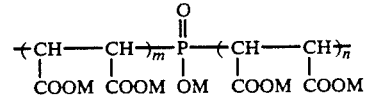

wherein G exceeds 32 mole percent, M is chosen, at each occurrence, from H, Na, K, NH4; and m and n are either 0 or a small whole number and the sum of m plus n is greater than 2.

In a preferred embodiment G is about between 35–40 mole percent. In most instances, M will be Na, or mixtures of H and Na.

As indicated, the above structure is considered to be probable, since due to the nature of the reactants, there is a possibility that a small amount of oligomer would contain random phosphorus atoms in the chain. Also it is known that the compounds related to the above oligomer tend to decarboxylate in the presence of strong oxidizing agents such as peroxides. Neutralization of the phosphinate product at the time of production or formulation into a water treatment composition has been demonstrated to minimize such decarboxylation.

As previously stated the active chelant or scale inhibitor is the oligomer. As will be shown hereafter, when compositions are prepared without oligomer present, they possess poor scale inhibiting properties. The improved scale inhibiting compositions afforded by the invention should contain more than 32 mole percent of the oligomer. Higher oligomer content, e.g., between 35–40 mole percent, gives the best scale inhibition results. The preferred method of making the compositions with high oligomer contents seems to be limited to producing materials having an oligomer content not much greater than 40 mole percent.

The high oligomer-containing compositions of the invention are prepared using the preparative technique set forth in U.S. Pat. No. 4,088,678, and the disclosure of which is incorporated herein by reference. Also incorporated by reference is the disclosure of GB No. 1,521,440. In using the preparative techniques of these patents it is necessary to react at greater than 2.2, but less than 3 moles of maleic acid or its equivalent salts, anhydride or esters with one mole of sodium or other water-soluble hypophosphite in order to produce the high oligomer-containing compositions. A preferred ratio of maleic acid to water-soluble hypophosphite is between 2.3–2.5, but less than 3 moles.

The high oligomer-containing products are only capable of being produced when the maleic acid is in excess to the hypophosphite during the course of the reaction. When the maleic acid is added to the hypophosphite incrementally, or continuously over a period of time, poor yields of the oligomer are obtained. As stated, the preparative technique set forth in U.S. Pat. No. 4,088,678 may be used. The compositions as produced are aqueous solutions containing between about 35–40% solids. To illustrate typical preparative techniques, the following procedure is presented:

PREPARATION OF HIGH OLIGOMER CONTENT PRODUCT

Maleic anhydride (306.25 g, 3.125 moles) briquettes were crushed and added to a 1.5 liter reaction flask along with about 516.9 g of water. The suspension was stirred for about fifteen (15) minutes as the maleic anhydride dissolved and hydrolyzed, raising the temperature of the solution from 21° C. to 32° C. After stirring for forty-five (45) minutes longer, the mild exotherm began to subside and sodium hypophosphite monohydrate (132.5 g, 1.25 moles) was added. A second mild exotherm occured as sodium hypophosphite was dissolved. Nitrogen purging was begun and the reaction mixture was heated to 60° C. over thirty (30) minutes. Ammonium persulfate solution was added (99.75 g of 37.22% aqueous solution) over about four (4) hours. Temperature was controlled at 60°–61° C. using heating or cooling as needed. When addition of the catalyst was complete, heating at 60° C. was continued for two and one-half (2.5) hours longer. Heating was continued and incrementally increased to 80° C. until oxidant was consumed or destroyed, as indicated by a negative starch-iodide test. The clear, yellow solution was highly acidic (pH 1). The concentration of the final product before neutralization was 44.77% (assuming complete incorporation of maleic acid and sodium hypophosphite). Analysis of the reaction mixture was done using $^{31}P$ and $^{13}C$ NMR, showing the absence of maleic acid in the final product mixture.

A sample (100.0 g of the 44.77% solution described above) was neutralized to pH 7.0 by dropwise addition of the fifty percent (50%) sodium hydroxide. Temperature of the solution was observed and maintained at 60° C. or less with ice-water bath cooling. The concentration of the resultant solution was 30.79% (calculated based on dilution).

Using the above preparative technique as well as what may be referred to as a semi-batch procedure, in which the maleic acid was added simultaneously with the initiator, a variety of product compositions were prepared. The results of these preparations are set forth below in Table I.

TABLE I

REACTIONS OF SODIUM HYPOPHOSPHITE WITH MALEIC ACID AND MALEATES
$^{31}P$ NMR ANAL, Mole Percent Phosphorus Compound

| Sample Number | Mole Ratio Mal./Hypo | Procedure | 2:1 | OLIG | 1:1 | PSA | Other Phosphon | Resid. | Comments |
|---|---|---|---|---|---|---|---|---|---|
| 1 | 2.2:1 | Addn. of APS to M.A. & NaH$_2$PO$_2$ | 19.0 | 27.6 | 23.2 | 13.4 | 5.3 | 11.5 | |
| 2 | 2.2:1 | Addn. of APS to M.A. & NaH$_2$PO$_2$ | 18.6 | 26.2 | 37.4 | 6.2 | 2.0 | 9.6 | |
| 3 | 2.2:1 | Addn. of APS to M.A. & NaH$_2$PO$_2$ | 19.0 | 31.7 | 25.6 | 9.7 | 4.0 | 10.0 | |
| 4 | 2.2:1 | Addn. of APS to M.A. & NaH$_2$PO$_2$ | 21.9 | 32.9 | 25.9 | 8.9 | 3.6 | 6.8 | |
| 5 | 2.2:1 | Addn. of M.A. to APS & NaH$_2$PO$_2$ | 52.3 | 24.0 | 16.7 | 3.3 | 0.0 | 3.7 | |
| 6 | 2.0:1 | Addn. of M.A. and APS to NaH$_2$PO$_2$ | 49.6 | 15.1 | 31.0 | 1.5 | 1.0 | 2.8 | Unreacted M.A. in sample |
| 7 | 2.0:1 | Addn. of M.A. and APS to NaH$_2$PO$_2$ | 57.4 | 13.5 | 20.6 | 3.6 | 0.9 | 4.0 | |
| 8 | 2.5:1 | Addn. of M.A. and APS to NaH$_2$PO$_2$ | 53.6 | 14.2 | 25.8 | 1.7 | 0.0 | 4.7 | Unreacted M.A. in sample |
| 9 | 2.5:1 | Addn. of APS to M.A. & NaH$_2$PO$_2$ | 17.6 | 40.5 | 22.0 | 9.0 | 4.9 | 6.0 | |
| 10 | 3.0:1 | Addn. of APS to M.A. & NaH$_2$PO$_2$ | 15.4 | 40.6 | 20.2 | 10.8 | 5.4 | 7.6 | Unreacted M.A. in sample |

TABLE I-continued

REACTIONS OF SODIUM HYPOPHOSPHITE WITH MALEIC ACID AND MALEATES
31P NMR ANAL, Mole Percent Phosphorus Compound

| Sample Number | Mole Ratio Mal./Hypo | Procedure | 2:1 | OLIG | 1:1 | PSA | Other Phosphon | Resid. | Comments |
|---|---|---|---|---|---|---|---|---|---|
| 11 | 2.0:1 | Addn. of APS and $NaH_2PO_2$ to M.A. | 14.8 | 27.2 | 31.4 | 3.5 | 6.1 | 17.0 | |
| 12 | 2.2/1.0 | Addn. of M.A. and APS to $NaH_2PO_2$ | 10.4 | 6.3 | 77.5 | 1.4 | 0.0 | 4.4 | Used Na maleate, some unreacted acid in sample |
| 13 | 2.0/1.0 | Addn. of Dimethyl maleate & t-butyl peroctoate to $NaH_2PO_2$ | 88.5 | 0.0 | 11.5 | 0.0 | 0.0 | 0.0 | EtOH + $H_2O$ solvent, ester saponified |
| 14 | 1.0/1.0 | Addn. of Dimethyl maleate & t-butyl peroctoate to $NaH_2PO_2$ | 8.1 | 0.0 | 73.8 | 0.0 | 0.0 | 18.1 | EtOH + $H_2O$ solvent, ester saponified |
| 15 | 1.0/1.0 | Addn. of M.A. and APS to $NaH_2PO_2$ | 12.8 | 0.0 | 67.1 | 0.0 | 0.0 | 20.1 | |
| 16 | 2.0/1.0 | Addn. of M.A. and V-50 to $NaH_2PO_2$ | 10.9 | 22.9 | 41.3 | 2.7 | 1.7 | 20.5 | |
| 17 | | Oxidation of Sample No. 7 with $H_2O_2$ | 68.0 | 3.0 | 0.0 | 26.0 | 0.0 | 3.0 | Sample No. 7 oxidized with $H_2O_2$ |

GLOSSARY
M.A. = Maleic acid
APS = Ammonium persulfate
Hypo = sodium hypophosphite monohydrate
2:1 = Monosodium phosphinicobis (succinate)
OLIG = Oligomeric phosphinicosuccinates
1:1 = Monosodium phosphinicosuccinate
V-50 = 2,2'-azobis (2-amidopropane) hydrochloride
PSA = Monosodium phosphonosuccinic
Other Phosphonics = Unknown phosphonic compounds
Resid. = Unreacted sodium hypophosphite and phosphorus acids The compositions used in the practise of the invention are in the form of aqueous solutions which have been neutralized with a water-soluble base such as sodium hydroxide to prevent decarboxylation from occurring. These neutralized compositions usually will be neutralized to a pH of around 7-7.5.

While these compositions of the invention are capable of providing good scale protection in a variety of industrial areas, they are most effective in providing protection to the surfaces in contact with alkaline cooling waters. These waters are most often cooled by means of large atmospheric cooling towers. Such waters are treated so that their pHs are within the range of between 8.2-9.5. Higher or lower alkaline pHs can be found in certain systems.

The dosage at which the compositions provide scale protection will vary depending upon the environment at which they are used. Based on total solids of the compositions, the dosage can be varied between 0.1-500 ppm based on the water being treated. A typically preferred dosage range is between 2.5-100 ppm.

EXAMPLE 1

Several of the compositions set forth in the above table were evaluated as scale inhibitors using the following test method, referred to as the "DEAL" technique, e.g. The Dynamic Equilibrium Alkalinity Limit.

The apparatus is recirculating system with a stainless steel heat transfer surface, outfitted with an automatic sampling system. The concentration of the ionic species is increased by evaporative water loss over a period of twenty-four (24) hours. On the basis of the chloride concentration, the cycles of concentration are determined. The desired product dosage is introduced to the system initially, here at a level of 10 ppm based on actives. By comparison of the observed soluble (filtered) calcium concentration with the theoretical concentration of calcium, an index of precipitation can be evaluated.

Two parameters are employed to characterize performance. The area of deviation between the theoretical and observed soluble calcium levels is integrated, as a measure of the total amount of precipitation. In addition, the maximum number of cycles which can be obtained before precipitation occurs characterizes inhibitor performance. A model has been developed to predict the potential $CaCO_3$ precipitation as a function of increasing concentration under the conditions of the test. The maximum $CaCO_3$ concentration where 95% of this precipitation has been inhibited is reported as a second measurement of the inhibitor's performance.

Using the DEAL method described above, the following test results were obtaining and are set forth in Table II.

TABLE II

| | $CaCO_3$ Scale Inhibition for Phosphinico- and Phosphonosuccinate Mixtures | | |
|---|---|---|---|
| Sample Number | Mole % Oligomer | Precipitation Area | Max $CaCO_3$ Inhibition (mg/l) |
| None | — | 374 | — |
| 15 | 0 | 307 | <268 |
| 13 | 0 | 306 | <273 |
| 17 | 3 | 164 | 342 |
| 7 | 14 | 148 | 352 |
| 3 | 32 | 78 | 374 |
| 9 | 40 | 60 | 393 |

In this Table, Precipitation Area means a computation of $CaCO_3$ precipitated during the test (for twenty (20) hours) while concentrating the initial water to two cycles. The lower the value, the more effective the initial inhibitor. Maximum $CaCO_3$ inhibition means the maximum calcium carbonate concentration where 95% of potential precipitation has been inhibited. The higher the value, the more effective is the inhibitor.

It is evident from a study of the data in Table II that unless the oligomer is present in the composition, there is poor scale inhibition. As a corollary, as the oligomer content increases, the scale inhibition increases.

When the oligomeric phosphinicosuccinic acid compound content is maximized, $CaCO_3$ inhibition activity of this mixture is equal to or better than the commerical low molecular weight polyacrylic acid, Goodrite K-752. This conclusion is reported in Table III.

TABLE III

CaCO$_3$ Scale Inhibition for
Phosphinico- and Phosphonosuccinates
Supersaturation - Titration Results[1]

| Sample Number | Mole % Oligomer | TITRATION DATA SATURATION RATIOS[2] DOSAGES | | |
|---|---|---|---|---|
| | | 5 ppm | 10 ppm | 15 ppm |
| 9 | 40 | 85.4 | 116.8 | 119.9 |
| 3 | 32 | 69.9 | 107.5 | 119.9 |
| 7 | 14 | 39.9 | 65.2 | 91.1 |
| Goodrite K-752 | — | 80.0 | 113.7 | 128.9 |

Test Conditions: 360 ppm Ca as CaCO$_3$
200 ppm Mg as CaCO$_3$
500 ppm HCO$_3$ as CaCO$_3$
Temperature - 60° C.
Stirring Rate - 300 rpm

[1]Solution of Ca$^{+2}$, Mg$^{++}$, HCO$_3$, and inhibitor are titrated with NaOH until supersaturation pH point for CaCO$_3$ precipitation is exceeded.
[2]Saturation Ratio - Ratio for number of times saturation point for CaCO$_3$ in test water is exceeded in presence of inhibitor test conditions. Higher values indicate better performance.

The compositions after neutralization are concentrated solutions containing substantial quantities of the oligomer and having a nearly neutral pH. These solutions may be used alone to prevent or to remove scale, but in many instances it is desirable to combine them with other treatments to provide a more versatile product.

Thus, they may be combined with other scale inhibitors and/or dispersants such as the low molecular weight polyacrylic acids. They may be combined with corrosion inhibitors such as the inorganic molecularly dehydrated phosphates. Similarly, they can be fortified with scale inhibiting organophosphonates to provide products having synergistic properties.

The oligomer-containing compositions described, in addition to preventing scale, have the potential for dispersing scale-forming components in scale-forming waters. This is so since the oligomers are low molecular weight and polymeric in nature. Also, they should be capable of removing existing scale when it is present on equipment surfaces, particularly heat transfer surfaces. When this use of composition is contemplated, high dosages should be employed.

Having thus described our invention, it is claimed as follows:

1. A method for controlling the deposition of calcium carbonate scale on the structural parts of a system exposed to alkaline cooling water containing calcium carbonate under deposit-forming conditions, which method comprises adding to said cooling water an effective amount of phosphinate-containing composition comprising:

| Ingredients | | Mole Percent - Less Than |
|---|---|---|
| A. | Monosodium phosphinicobis-(succinic acid) | 22 |
| B. | Monosodium phosphinico-succinic acid | 26 |
| C. | Sodium phosphonosuccinic acid | 12 |
| D. | Sodium phosphate | 5 |
| E. | Sodium phosphite | 6 |
| F. | Sodium hypophosphite, and | 6 |
| G. | A phosphinicosuccinic acid oligomer having the structural formula: | |

$$\left(\text{CH}-\text{CH}\right)_m-\overset{\overset{\displaystyle O}{\|}}{P}-\left(\text{CH}-\text{CH}\right)_n$$
$$\underset{\text{COOM COOM}}{|\quad\quad |}\quad \underset{\text{OM}}{|}\quad \underset{\text{COOM COOM}}{|\quad\quad |}$$

wherein G exceeds 32 mole percent, M is chosen, at each occurrence, from H, Na, K, NH$_4$; and m and n are either 0 or a whole number and the sum of m plus n is greater than 2, wherein said composition is formed by reacting greater than 2.2, but less than 3 moles of maleic acid or its equivalent salts, anhydride, or esters with one mole of sodium or other water-soluble hypophosphite.

2. The method of claim 1 wherein the ingredients of the phosphinate-containing composition G is about between 35–40 mole percent.

3. The method of claim 1 wherein the ingredients of the phosphinate-containing composition M is from the group H and Na, and mixtures thereof.

* * * * *

UNITED STATES PATENT AND TRADEMARK OFFICE
CERTIFICATE OF CORRECTION

PATENT NO. : 5,023,000

DATED : June 11, 1991

INVENTOR(S) : James F. Kneller, et al

It is certified that error appears in the above-identified patent and that said Letters Patent is hereby corrected as shown below:

ON TITLE PAGE: Item [54] and in column 1.

Title of Invention:

"OLIGOMER-CONTAINING PHOSPHATE SCALE INHIBITORS"

Title of Invention Should Read As:

"OLIGOMER-CONTAINING PHOSPHINATE SCALE INHIBITORS"

Signed and Sealed this

Twenty-ninth Day of September, 1992

Attest:

DOUGLAS B. COMER

*Attesting Officer*    *Acting Commissioner of Patents and Trademarks*